US011077179B2

(12) United States Patent
Gillis

(10) Patent No.: US 11,077,179 B2
(45) Date of Patent: Aug. 3, 2021

(54) METHOD FOR TREATING FIBROMYALGIA AND CHRONIC FATIGUE SYNDROME

(71) Applicant: EpicGenetics, Inc., Los Angeles, CA (US)

(72) Inventor: Bruce S. Gillis, Beverly Hills, CA (US)

(73) Assignee: EPICGENETICS, INC., Los Angeles, CA (US)

( * ) Notice: Subject to any disclaimer, the term of this patent is extended or adjusted under 35 U.S.C. 154(b) by 0 days.

(21) Appl. No.: 16/055,565

(22) Filed: Aug. 6, 2018

(65) Prior Publication Data

US 2019/0046628 A1 Feb. 14, 2019

Related U.S. Application Data

(60) Provisional application No. 62/543,478, filed on Aug. 10, 2017, provisional application No. 62/642,621, filed on Mar. 14, 2018.

(51) Int. Cl.

| | |
|---|---|
| ***A61K 39/04*** | (2006.01) |
| ***A61P 21/00*** | (2006.01) |
| ***A61K 9/00*** | (2006.01) |
| *A61K 39/00* | (2006.01) |

(52) U.S. Cl.

CPC .............. *A61K 39/04* (2013.01); *A61P 21/00* (2018.01); *A61K 9/0019* (2013.01); *A61K 2039/521* (2013.01); *A61K 2039/522* (2013.01); *A61K 2039/54* (2013.01); *A61K 2039/545* (2013.01); *A61K 2039/58* (2013.01)

(58) Field of Classification Search

None

See application file for complete search history.

(56) References Cited

U.S. PATENT DOCUMENTS

| | | | | |
|---|---|---|---|---|
| 6,368,590 | B1 | 4/2002 | Gottfries et al. | |
| 8,071,354 | B2 * | 12/2011 | Stanford | A61P 25/22 435/252.1 |
| 8,557,257 | B2 * | 10/2013 | Morton | A61K 35/74 424/234.1 |
| 2003/0170275 | A1 | 9/2003 | Rook et al. | |
| 2005/0118201 | A1 * | 6/2005 | Wright | A61K 39/04 424/248.1 |
| 2009/0012009 | A1 * | 1/2009 | Low | A61K 31/519 514/6.9 |
| 2011/0000480 | A1 * | 1/2011 | Turner | A61K 38/212 128/200.23 |
| 2012/0258135 | A1 * | 10/2012 | Gunn | A61K 39/0008 424/206.1 |
| 2015/0246080 | A1 | 9/2015 | Akle et al. | |
| 2015/0301062 | A1 | 10/2015 | Gillis | |
| 2016/0024476 | A1 | 1/2016 | Belnoue et al. | |
| 2020/0064356 | A1 | 2/2020 | Gillis | |

FOREIGN PATENT DOCUMENTS

| | | | | |
|---|---|---|---|---|
| EP | 0951289 B1 | | 10/1999 | |
| WO | WO85/05034 | | 11/1985 | |
| WO | WO-0110221 A1 | * | 2/2001 | A61K 39/04 |
| WO | WO-2015057968 A2 | * | 4/2015 | G01N 33/505 |
| WO | WO-2017059132 A1 | * | 4/2017 | G01N 33/48 |

OTHER PUBLICATIONS

Zhang et al. Molecular Therapy 24(2):398-405, 2016 (Year: 2016).*
Bottai et al. Mol. Ther. Feb. 2016; 24 (2):201-203.*
Kreider et al. Cancer 46:480-487, 1980.*
Stanford et al. Immunotherapy (2011) 3(4), 557-568.*
Wallace et al. Rheumatol Int (2015) 35:991-996.*
Behm et al. BMC Clinical Pathology 2012, 12:25, 7 pages.*
Andersson et al., "Effects of *Staphylococcus* toxoid vaccine on pain and fatigue in patients with fibromyalgia/chronic fatigue syndrome," Eur J Pain. 1998; 2(2): 133-142.
Zachrisson et al., "Treatment with *Staphylococcus* toxoid in fibromyalgia/chronic fatigue syndrome—a randomised controlled trial," Eur J Pain. 2002; 6(6): 455-466.
BusinessWire, Apr. 19, 2017, "EpicGenetics, with the Assistance of Leading Medical Centers, Expands Clinical Study of FM/a Test to Diagnose Fibromyalgia, Identify Genetic Markers Unique to the Disorder and Explore Direct Treatment Approaches—Provides Research Gift to the Faustman Immunobiology Lab at Massachusetts General Hospital/Harvard Medical School to Support Research on Fibromyalgia Treatments," 3 pages.
Barreto, et al., "BCG vaccine: efficacy and indications for vaccination and revaccination," J Pediatr (Rio J). 2006;82(3 Suppl):S45-54.
Grode, et al., "Increased vaccine efficacy against tuberculosis of recombinant *Mycobacterium bovisbacille* Calmette-Guerin mutants that secrete listeriolysin," The Journal of Clinical Investigation 115(9):2472-2479 (2005).
Dalgleish, et al., Randomised, open-label, phase II study of gemcitabine with and without IMM-101 for advanced pancreatic cancer, British Journal of Cancer (2016), pp. 1-8.
Maraveyas et al., "Possible improved survival of patients with stage IV AJCC melanoma receiving SRL 172 immunotherapy: Correlation with induction of increased levels of intracellular interleukin-2 in peripheral blood lymphocytes," Annals of Oncology 10:817-824 (1999), downloaded from http://annonc.oxfordjournals.org on Jan. 4, 2017.
Stebbing et al., "An intra-patient placebo-controlled phase I trial to evaluate the safety and tolerability of intradermal IMM-101 in melanoma," Annals of Oncology 23:1314-1319 (2012), downloaded from http://annonc.oxfordjournals.org/ on Sep. 19, 2016.
Zachrisson et al., "A rating scale for fibromyalgia and chronic fatigue syndrome (the FibroFatigue scale).," J Psychosom Res. Jun. 2002;52(6):501-509.

* cited by examiner

*Primary Examiner* — Oluwatosin A Ogunbiyi
(74) *Attorney, Agent, or Firm* — Cooley LLP

(57) ABSTRACT

The invention provides methods and compositions for treating fibromyalgia (FM) and chronic fatigue syndrome (CFS) in an individual. The methods provided herein entail administering a composition comprising an isolated *Mycobacterium* or antigenic fragments derived therefrom. Also provided herein are methods for assessing alleviation of symptoms and/or alteration of immune system functioning following administration of a composition comprising an isolated *Mycobacterium* or antigenic fragments derived therefrom.

10 Claims, No Drawings

METHOD FOR TREATING FIBROMYALGIA AND CHRONIC FATIGUE SYNDROME

CROSS REFERENCE TO RELATED APPLICATIONS

This application claims benefit from U.S. Provisional Application No. 62/543,478, filed Aug. 10, 2017, and U.S. Provisional Application No. 62/642,621, filed Mar. 14, 2018, each of which is incorporated by reference herein in its entirety for all purposes.

FIELD OF THE INVENTION

This invention provides methods for treating fibromyalgia and chronic fatigue syndrome (CFS) using compositions comprising isolated Mycobacteria or antigenic fragments derived therefrom. Provided herein are also methods for diagnosing CFS by measuring levels of one or more select cytokines.

BACKGROUND OF THE INVENTION

Fibromyalgia (FM) or FM syndrome is a medical disorder of unknown etiology characterized by chronic widespread joint and muscle pain. Other symptoms include allodynia (a heightened and painful response to pressure), debilitating fatigue, sleep disturbance, and joint stiffness, numbness, tingling and cognitive dysfunction. The etio-pathophysiology of FM is not entirely understood, although inflammation in the musculoskeletal system of FM patients shows that the immune system plays a role in the etio-pathophysiology of FM. In addition, genetic and environmental factors have been suggested to play a role in the etio-pathophysiology of FM.

This debilitating, chronic affliction affects 10 million Americans and there is no known cure for the disease. Although fibromyalgia does not have a specific treatment or treatment paradigm, three medications have been approved by the FDA for the treatment of fibromyalgia. These are pregabalin (Lyrica®), duloxetine (Cymbalta®), and milnacipran (Savella®). However, recent research indicates that current treatments are really not effective in the reduction of pain or improvement in function in patients with fibromyalgia, and there is still a lack of effective drugs for the treatment of fibromyalgia over time (Wolfe et al., 2012, "Longitudinal Patterns of Analgesic and Central Acting Drug Use and Associated Effectiveness in Fibromyalgia," *Eur. J. Pain* 17(4): 581-86).

Accordingly, there is a need for a treatment of FM that has long lasting effects on a majority or all of the symptoms associated with FM. The present invention addresses this and other needs.

Chronic fatigue syndrome (CFS) (also referred to as myalgic encephalomyelitis (ME) or systemic intolerance disease (SEID)) is a serious, debilitating condition that affects somewhere between 836,000 and 2.5 million Americans. CFS is a clinically defined condition characterized by severe disabling flu-like fatigue following exertion of any sort (physical, cognitive or emotional) as well as a combination of symptoms that include reduction or impairment in ability to carry out normal daily activities, cognitive impairment (e.g., impairment of concentration and short-term memory), sleep disturbances (unrefreshing sleep), and orthostatic intolerance (symptoms that worsen when a person stands upright and improve when the person lies back down). Other common manifestations include musculoskeletal pain, failure to recover from a prior infection, abnormal immune function. Further, symptoms can persist for years with one-quarter of ME/CFS patients being bed or house bound at some point in their illness and most patients never regaining their pre-disease level of health or functioning. Overall, ME/CFS patients can experience a loss of productivity as well as high medical costs that contribute to a total economic burden of $17 to $24 billion annually.

Currently, the cause of ME/CFS remains unknown, although there is some evidence that symptoms may be triggered by certain infections. Further, no specific test exists to diagnose chronic fatigue syndrome and there is no existing cure for ME/CFS. While there are therapies available to manage symptoms, the efficacy of said therapies is largely unknown.

Accordingly, there is a need for a treatment of CFS that has long lasting effects on a majority or all of the symptoms associated with CFS. The present invention addresses this and other needs.

SUMMARY OF THE INVENTION

In one aspect, provided herein is a method of treating or preventing fibromyalgia in a subject, comprising administering a therapeutically effective amount of a vaccine to the subject, wherein the vaccine comprises *Mycobacterium bovis* or an antigenic fragment thereof. In some cases, the *M. bovis* is live-attenuated. In some cases, the *M. bovis* is heat-killed. In some cases, the *M. bovis* is a Bacille Calmette-Guerin (BCG) strain. In some cases, the BCG strain belongs to duplication group DU1, DU2-I, DU2-II, DU2-III or DU2-IV. In some cases, the BCG strain is a sub-strain selected from BCG Pasteur (1961), BCG Moreau, BCG Tokyo, BCG Russia (1924), BCG Japan (1925), BCG Sweden (1927), BCG Birkhaug, BCG Prague, BCG Glaxo (1954), BCG Merieux (1989), BCG Danish, BCG Frappier, BCG Connaught (1948), BCG Mexico, BCG Tice (1934), BCG China or BCG Phipps. In some cases, the BCG strain is BCG Tokyo. In some cases, the vaccine further comprises an adjuvant. In some cases, the vaccine induces one or more epigenetic changes in the genome of the subject. In some cases, the vaccine is administered in repeat doses. In some cases, the vaccine is administered in a unit dose comprising $1.8\times10^6$ to $3.9\times10^6$ colony forming units/injection of 0.1 ml. In some cases, the vaccine is formulated for intradermal administration. In some cases, the administration of the vaccine alleviates, prevents or reduces at least one sign or symptom of fibromyalgia, wherein the sign or symptom is selected from chronic muscle pain, muscle spasms, muscle tightness, moderate or severe fatigue, decreased energy, insomnia, feeling of exhaustion, stiffness upon waking, stiffness after staying in one position for too long, difficulty remembering, difficulty concentrating, difficulty performing simple mental tasks ("fibro fog"), abdominal pain, bloating, nausea, constipation alternating with diarrhea (irritable bowel syndrome), tension or migraine headaches, jaw and facial tenderness, sensitivity to one or more of odors, noise, bright lights, medications, certain foods, and cold, feeling anxious or depressed, numbness or tingling in the face, arms, hands, legs, or feet, increase in urinary urgency or frequency (irritable bladder), reduced tolerance for exercise and muscle pain after exercise, a feeling of swelling (without actual swelling) in the hands and feet or any combination of symptoms thereof. In some cases, the administration of the vaccine elevates or increases immune system activity of the subject. In some cases, the elevation or increase in immune system function is evidenced by the production of $T_H1$ cytokines, upregulation of granzyme B or both.

In another aspect, provided herein is a method of elevating or increasing a subject's immune system function comprising administering a therapeutically effective amount of a vaccine to the subject, wherein the subject suffers from or is suspected of suffering from fibromyalgia and wherein the vaccine comprises *Mycobacterium bovis* or an antigenic fragment thereof. In some cases, the elevation or increase in immune system function is evidenced by the production of $T_H1$ cytokines, upregulation of granzyme B or both. In some cases, the elevation or increase in immune system function is evidenced by a reduction or alleviation of at least one sign or symptom of fibromyalgia. In some cases, the sign or symptom of fibromyalgia is selected from chronic muscle pain, muscle spasms, muscle tightness, moderate or severe fatigue, decreased energy, insomnia, a feeling of exhaustion, stiffness upon waking, stiffness after staying in one position for too long, difficulty remembering, difficulty concentrating, difficulty performing simple mental tasks ("fibro fog"), abdominal pain, bloating, nausea, and constipation alternating with diarrhea (irritable bowel syndrome), tension or migraine headaches, jaw and facial tenderness, sensitivity to one or more of odors, noise, bright lights, medications, certain foods, and cold, feeling anxious or depressed, numbness or tingling in the face, arms, hands, legs, or feet, increase in urinary urgency or frequency (irritable bladder), reduced tolerance for exercise and muscle pain after exercise. a feeling of swelling (without actual swelling) in the hands and feet or a combination of symptoms thereof. In some cases, the vaccine induces one or more epigenetic changes in the genome of the individual. In some cases, the vaccine is live-attenuated. In some cases, the vaccine is heat-killed. In some cases, the *M. bovis* is a Bacille Calmette-Guerin (BCG) strain. In some cases, the BCG strain belongs to duplication group DU1, DU2-I, DU2-II, DU2-III or DU2-IV. In some cases, the BCG strain is a sub-strain selected from BCG Pasteur (1961), BCG Moreau, BCG Tokyo, BCG Russia (1924), BCG Japan (1925), BCG Sweden (1927), BCG Birkhaug, BCG Prague, BCG Glaxo (1954), BCG Merieux (1989), BCG Danish, BCG Frappier, BCG Connaught (1948), BCG Mexico, BCG Tice (1934), BCG China or BCG Phipps. In some cases, the BCG strain is BCG Tokyo. In some cases, the vaccine further comprises an adjuvant. In some cases, the vaccine is administered in repeat doses. In some cases, the vaccine is administered in a unit dose comprising $1.8\times10^6$ to $3.9\times10^6$ colony forming units/injection of 0.1 ml. In some cases, the vaccine is formulated for intradermal administration.

DETAILED DESCRIPTION OF THE INVENTION

Definitions

Unless otherwise defined, all technical terms used herein have the same meaning as commonly understood by one of ordinary skill in the art to which this invention belongs.

While the following terms are believed to be well understood by one of ordinary skill in the art, the following definitions are set forth to facilitate explanation of the presently disclosed subject matter.

The term "a" or "an" refers to one or more of that entity, i.e. can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, "protein" and "polypeptide" are used synonymously to mean any peptide-linked chain of amino acids, regardless of length or post-translational modification, e.g., glycosylation or phosphorylation.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458.

For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual ($3^{rd}$ ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

The term "cytokine" as used herein refers to small proteins that are secreted by specific cells of the immune system and glial cells, and include lymphokines, interleukins, and chemokines and their corresponding receptors, such as but not limited to IL-1, IL-2, IL-4, IL-5, IL-6, IL-7, IL-8, IL-10, IL-12, IL-13, IL-15, IL-17, IL-21, IFN-γ, IFN-α, TNF-α, IP-10, MCP-1, MIG, MIP-1α, MIP-1β, GM-CSF, Eotaxin, RANTES, etc. In another aspect, the invention further includes determining the levels of one or more of IL-1RA, IL2R, IL-7, IL-12 (p40/p70), IL-13, IL-15, IL-17, IFN-α, IP-10, MIG, VEGF, G-CSF, EGF, FGF-basic and HGF. In yet another aspect, the invention also includes determining the levels of IL-9 and PDGF-BB or a combination thereof. The cytokine may be inflammatory or anti-inflammatory. In one embodiment, the cytokine to be assayed may be a full length polypeptide, protein, a glycoprotein or a fragment thereof. Other proteins that can be assayed include hormones, heat-shock proteins, antibodies such as but not limited to anti-nuclear antibody (ANA), thyroid antibodies, anti-extractable nuclear antibodies (ENA), IgG subclasses, anti-nuclear factors (FAN), rheumatoid factor (RF), receptor proteins and ligands, etc. In other embodiment, the level of cytokine assayed maybe a mRNA, miRNA, or DNA.

As used herein, the term "treatment" is defined as the application or administration of a therapeutic agent described herein, or identified by a method described herein, to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

The terms "patient", "subject" and "individual" are used interchangeably herein, and mean a mammalian subject to be treated, with human patients being preferred. In some cases, the methods of the invention find use in experimental animals, in veterinary applications, and in the development of animal models for disease, including, but not limited to, rodents including mice, rats, and hamsters, as well as primates.

By the phrases "therapeutically effective amount" and "effective dosage" is meant an amount sufficient to produce a therapeutically (e.g., clinically) desirable result; the exact nature of the result will vary depending on the nature of the disorder being treated. For example, where the disorder to be treated is fibromyalgia (FM), the result can be an alleviation of one or more symptoms of FM such as, for example, widespread pain. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions of the invention can include a single treatment or a series of treatments.

Overview

The present invention provides compositions and methods for treating fibromyalgia (FM) in an individual. In one embodiment, treating FM in an individual comprises administering a vaccine. The vaccine can be any vaccine that can induce epigenetic changes in an individual administered said vaccine. The epigenetic changes can serve to provide the individual with life-long immunity against re-occurrence of FM. The epigenetic changes can be cis-acting or trans-acting. The epigenetic changes can include changes in DNA methylation and/or histone protein modification. The vaccine can induce a chemokine and/or cytokine response in the individual. The epigenetic changes or modifications can impact the chemokine and/or cytokine responses in the individual. The vaccine composition can comprise a *Mycobacterium* or an antigenic fragment thereof. The *Mycobacterium* can be an isolated *Mycobacterium* or an antigenic fragment thereof. In one embodiment, the *Mycobacterium* is a Bacille Calmette-Guerin (BCG) strain of *Mycobacterium bovis* (*M. bovis*). Further to this embodiment, the composition can be a BCG vaccine. The BCG vaccine can be any BCG vaccine known in the art and/or commercially available. In a preferred embodiment, the BCG vaccine comprises the Tokyo 172 strain of BCG (e.g., Type I or Type II). The BCG vaccine can be live-attenuated or heat-killed. In another embodiment, the *Mycobacterium* is a non-pathogenic *Mycobacterium* species such as, for example *Mycobacterium vaccae* or *Mycobacterium* obtuense. The non-pathogenic *Mycobacterium* can be live-attenuated or heat-killed. The individual may have been previously diagnosed with FM or may be suspected of suffering from or being afflicted with FM. In one embodiment, the individual was previously diagnosed as having FM using any diagnostic means or methods known in the art such as, for example, the FM/a® Fibromyalgia test. In another embodiment, the individual was previously diagnosed as having FM using the methods disclosed in US20150301062A1, the contents of which are herein incorporated by reference in their entirety.

In one embodiment, the FM diagnosis can be determined by detecting the levels of one or more cytokines in a sample obtained from the individual to see if the levels of the one or more cytokines are altered. Further to this example, to determine whether cytokine levels are altered, the cytokine levels in the individual are compared to control cytokine levels, for example, cytokine levels from a healthy patient, or cytokine levels reported for a patient without fibromyalgia (for example, levels reported in a database). In one embodiment, a positive diagnosis of fibromyalgia is provided if a majority of the cytokines tested have altered expression. In a further embodiment, a positive diagnosis of fibromyalgia is provided if at least about 67% of the cytokines tested have altered expression, or at least about 67% or more of the cytokines tested have altered expression. In a further embodiment, a positive diagnosis of fibromyalgia is provided if at least about 75%, or at least about 75% or more of the cytokines tested have altered expression. In even a further embodiment, a positive diagnosis of fibromyalgia is provided if the expression level of every cytokine tested, or about every cytokine tested in the patient is altered. In one embodiment, altered expression is determined by comparing the cytokine levels of the individual's sample to control levels. Control levels, in one embodiment, are determined by testing a sample of an individual known to not have FM. In another embodiment, control levels are known, for example, from a database. The altered level(s) of the cytokines measured in the affected individual compared to the level from control group is predictive/indicative of FM in the individual. The cytokine levels in an individual with FM, for example, cytokine levels in a FM patient's blood, in one embodiment, are higher than the cytokine levels of a healthy patient, for each cytokine tested. In another embodiment, the cytokine levels in a FM patient's blood are lower than the cytokine levels of a healthy patient, for each cytokine tested. In yet another embodiment, the cytokine levels measured in a patient with FM may be higher or lower, depending on the panel of cytokines measured in the individual.

In one embodiment, the FM diagnosis can be determined by evaluating an individual suspected of suffering from FM with the FibroFatigue scale. The FibroFatigue scale is an observer's rating scale with 12 items measuring pain, muscular tension, fatigue, concentration difficulties, failing memory, irritability, sadness, sleep disturbances, and autonomic disturbances (items derived from the CPRS) and irritable bowel, headache, and subjective experience of infection as described in Zachrisson et al., J Psychosom Res. 2002 June; 52(6):501-9, which is herein incorporated by reference in its entirety. The FibroFatigue scale can be conducted by a trained administrator. In another embodiment, the FM diagnosis can be determined by evaluating an individual suspected of suffering from FM with the FibroFatigue Scale in combination with detecting the levels of one or more cytokines in a sample obtained from the individual to see if the levels of the one or more cytokines are altered as described herein.

The present invention also provides compositions and methods for treating chronic fatigue syndrome (CFS) in an individual. In one embodiment, treating CFS in an individual comprises administering a vaccine. The vaccine can be any vaccine that can induce epigenetic changes in an individual administered said vaccine. The epigenetic changes can serve to provide the individual with life-long immunity against re-occurrence of a disease or condition such as CFS. The epigenetic changes can be cis-acting or trans-acting. The epigenetic changes can include changes in DNA methylation and/or histone protein modification. The vaccine can induce a chemokine and/or cytokine response in the individual. The epigenetic changes or modifications can impact the chemokine and/or cytokine responses in the individual. The vaccine composition comprises a *Mycobacterium* or an antigenic fragment thereof. The *Mycobacterium* can be an isolated *Mycobacterium* or an antigenic fragment thereof. In one embodiment, the *Mycobacterium* is a Bacille Calmette-Guerin (BCG) strain of *Mycobacterium bovis* (*M. bovis*). Further to this embodiment, the composition can be a BCG vaccine. The BCG vaccine can be any BCG vaccine known in the art and/or commercially available. In a preferred embodiment, the BCG vaccine comprises the Tokyo 172 strain of BCG (e.g., Type I or Type II). The BCG vaccine can be live-attenuated or heat-killed. In another embodiment, the *Mycobacterium* is a non-pathogenic *Mycobacterium* species such as, for example *Mycobacterium vaccae* or *Mycobacterium obtuense*. The non-pathogenic *Mycobacterium* can be live-attenuated or heat-killed. The individual may have been previously diagnosed with CFS or may be suspected of suffering from or being afflicted with CFS. In one embodiment, the individual was previously diagnosed as having CFS using any diagnostic means or methods known in the art such as, for example, following an appropriate history, physical examination, and medical work-up. In one embodiment, the individual was previously diagnosed as having CFS using the commercially available FM/a® Fibromyalgia test. In another embodiment, the individual was previously diagnosed as having CFS using the methods disclosed in US20150301062A1, the contents of which are herein incorporated by reference in their entirety.

The CFS diagnosis can be determined following assessment of a subject's history, physical examination by a medical professional (e.g., physician) and a medical work-up. The CFS diagnosis can be assigned or determined if a subject experiences a specific set of symptoms that can be each of: 1.) a substantial reduction or impairment in the ability to engage in pre-illness levels of occupational, educational, social, or personal activities that persists for more than 6 months and is accompanied by fatigue, which is often profound, is of new or definite onset (not lifelong), is not the result of ongoing excessive exertion, and is not substantially alleviated by rest; 2.) post-exertional malaise; and 3.) unrefreshing sleep. A CFS diagnosis can be assigned if the subject experiences each of the aforementioned set of symptoms in combination with one or both of cognitive impairment and orthostatic intolerance. A positive CFS diagnosis can be ascribed to a subject if the subject experiences the aforementioned set of symptoms alone or in combination with cognitive impairment and/or orthostatic intolerance for at least 6 months. A positive CFS diagnosis can be ascribed to a subject if the subject experiences the aforementioned set of symptoms alone or in combination with cognitive impairment and/or orthostatic intolerance for at least 6 months and can be described as being chronic, frequent and/or moderate to severe in intensity. Other symptoms that a subject may experience can be pain, certain infectious diseases, gastrointestinal and genitourinary problems, sore or scratchy throat, painful or tender axillary/cervical lymph nodes, sensitivity to external stimuli, immune system problems, hormonal imbalances or any combination thereof. The certain infectious diseases can be viral infections with the Epstein-Barr virus, human herpes virus 6 (HHV-6), coxsackievirus B, spumaviruses, human T-cell leukemia virus strains, and/or mouse retroviruses. The certain infectious diseases can be pneumonia, diarrhea or upper respiratory tract infections. In some cases, diagnosis of CFS in a subject can comprise determining the presence and/or level of antibodies (e.g., IgGs) to antigens derived from one or more of the aforementioned viruses and/or *Chlamydia pneumoniae.*

In another embodiment, the CFS diagnosis can be determined by detecting the levels of one or more cytokines in a sample obtained from an individual to see if the levels of the one or more cytokines are altered. In one embodiment, the method comprises determining whether the levels of at least two, at least three, at least four, at least five, at least six, at least seven, at least eight, at least nine, at least ten, at least eleven, at least twelve or at least thirteen cytokines, or at least thirteen or more cytokines in an individual are altered. In one embodiment, the methods for diagnosing or predicting CFS in a patient involve determining or assaying the levels of at least one, at least two, at least three, at least four, at least five, at least six, at least seven, at least eight, at least nine, or at least ten or more cytokines in the plasma of blood samples obtained from individuals suspected of being afflicted with CFS or at risk for CFS. In a further embodiment, the method involves determining or assaying the levels of at least one, at least two, at least three, at least four, at least five, at least six, at least seven, at least eight, at least nine, or at least ten or more cytokines in the peripheral blood mononuclear cells (PBMCs) that have been separated from the plasma of blood samples obtained from the individuals. These levels are then analyzed to determine if the levels are altered. The alteration may be an increase or decrease in expression of a cytokine. The alteration can be determined at the protein and/or mRNA level as provided herein.

In one embodiment, altered expression is determined by comparing the cytokine levels of the individual's sample to control levels. Control levels, in one embodiment, are determined by testing a sample from a healthy individual or an individual known to not have CFS. In another embodiment, control levels are known, for example, from a database. The altered level(s) of the cytokines measured in the affected individual compared to the level from the control group is predictive/indicative of CFS in the individual. In one embodiment, a positive diagnosis of CFS is provided if at least about 33% of the cytokines tested have altered expression, or at least about 33% or more of the cytokines tested have altered expression. In another embodiment, a positive diagnosis of CFS is provided if a majority of the cytokines tested have altered expression. In a further embodiment, a positive diagnosis of CFS is provided if at least about 67% of the cytokines tested have altered expression, or at least about 67% or more of the cytokines tested have altered expression. In a further embodiment, a positive diagnosis of CFS is provided if at least about 75%, or at least about 75% or more of the cytokines tested have altered expression. In even a further embodiment, a positive diagnosis of CFS is provided if the expression level of every cytokine tested, or about every cytokine tested in the patient is altered. The sample can be a solid sample (e.g., tissue biopsy) or a liquid sample (e.g., blood sample or a fraction thereof). As described herein, altered expression can be an increase or decrease in expression. The altered expression can be at the protein and/or mRNA level as described herein.

The cytokine levels in an individual with CFS, for example, cytokine levels in a CFS patient's blood, in one embodiment, are higher than the cytokine levels of a healthy patient, for each cytokine tested. In another embodiment, the cytokine levels in a CFS patient's blood are lower than the cytokine levels of a healthy patient, for each cytokine tested. In yet another embodiment, the cytokine levels measured in a patient with CFS may be higher or lower, depending on the panel of cytokines measured in the individual.

The present invention is not limited by any particular combination of cytokines. For example, the expression levels of cytokines included in commercial cytokine panels (or cytokine subsets thereof) can be evaluated by the methods provided herein. Various combinations of cytokines for use in the present invention are provided in Table 1 below. Subsets of these combinations may also be used in the methods provided herein. It should be understood that these combinations are representative, and should not be construed as limiting the invention.

TABLE 1

Non-limiting cytokine panels for use with the present invention.

| Panel 1 | Panel 2 | Panel 3 | Panel 4 | Panel 5 |
|---|---|---|---|---|
| IL5 | IFN-γ | TranSignal | Bio-Plex Pro | five or more |
| IL6 | IL-1β | Human Cytokine | magnetic | chemokines |

TABLE 1-continued

Non-limiting cytokine panels for use with the present invention.

| | | | | |
|---|---|---|---|---|
| IL8 | IL-2 | Antibody Array | Cytokine Assay | |
| IL 10 | IL-4 | 3.0 (or a subset | (any of these | |
| IFN-γ | IL-5 | of cytokines | assays may be | |
| MCP-1 | IL-6 | provided in this | used, i.e., the | |
| MIP-1α | IL-8 | assay) | 8-plex, 17-plex, | |
| MIP-1β | IL-10 | | 21-plex, 27-plex | |
| | TNF-α | | | |
| | MIP-1β | | | |
| | MCP-1 | | | |
| | MIP-1α | | | |
| | Rantes | | | |

| Panel 6 | Panel 7 | Panel 8 | Panel 9 | Panel 10 |
|---|---|---|---|---|
| IL5 | IL-6 | IL-2 | IL-8 | IFN-γ |
| IL6 | IL-8 | IL-4 | IL-10 | IL-1β |
| IL8 | IL-10 | IL-5 | TNF-α | IL-2 |
| IL 10 | TNF-α | IL-6 | MIP-1β | |
| IFN-γ | MIP-1β | | MCP-1 | |
| | MCP-1 | | Rantes | |
| | MIP-1α | | | |

The present invention also provides compositions and methods for treating an individual suffering from or suspected of suffering from conditions that share many clinical illness features with FM and/or CFS or any comorbid illnesses. An example of conditions that shares clinical illness features of myalgia, fatigue, sleep disturbances and impairment in ability to perform activities of daily living is temporomandibular disorder (TMD). Examples of illnesses comorbid with FM and/or CFS can be irritable bowel sydrome (IBS), chronic tension-type headache and interstitial cystitis. The treatment can be a vaccine as provided herein.

In one embodiment, administration, as defined herein, includes the administration of the vaccine (e.g., *Mycobacterium* or an antigenic fragment thereof) in multiple aliquots and/or doses and/or on separate occasions. The vaccine can be a *Mycobacterium* vaccine. The *Mycobacterium* vaccine can comprise a *Mycobacterium* or an antigenic fragment thereof.

In one aspect of the present invention, the *Mycobacterium* comprises a live-attenuated strain of a Mycobacterial species or an antigenic fragment thereof. In another aspect of the present invention the *Mycobacterium* comprises heat-killed strain of a Mycobacterial species or an antigenic fragment thereof.

Mycobacterial species for use in the present invention include, but are not limited to *M. vaccae, M. thermoresistibile, M. flavescens, M. duvalii, M. phlei, M. obuense, M. parafortuitum, M. sphagni, M. aichiense, M. rhodesiae, M. neoaurum, M. chubuense, M. tokaiense, M. komossense, M. aurum, M. indicus pranii, M. tuberculosis, M. micron; M africanum; M. kansasii, M. marinum; M. simiae; M. gastri; M. nonchromogenicum; M. terrae; M. triviale; M. gordonae; M. scrofulaceum; M. paraffinicum; M. intracellulare; M. avium; M. xenopi; M. ulcerans; M. diemhoferi, M. smegmatis; M. thamnopheos; M. flavescens; M. fortuitum; M. peregrinum; M. chelonei; M. paratuberculosis; M. leprae; M. lepraemurium; M. bovis* and combinations thereof.

In one embodiment, the Mycobacterial species is *M. bovis*. The *M. bovis* can be any known strain of *M. bovis*. In one embodiment, the *M. bovis* is a BCG strain. The BCG can be heat-killed or live-attenuated. The BCG can be any known BCG vaccine. The strain of BCG can be any of the strains belonging to BCG groups DU1, DU2-I, DU2-II, DU2-III and DU2-IV. The strain of BCG can be selected from BCG Pasteur (1961), BCG Moreau, BCG Russia (1924), BCG Japan (1925), BCG Tokyo 172 (Type I, Type II) or a combination thereof, BCG Sweden (1927), BCG Birkhaug, BCG Prague, BCG Glaxo (1954), BCG Merieux (1989), BCG Danish, BCG Frappier, BCG Connaught (1948), BCG Mexico, BCG Tice (1934), BCG China or BCG Phipps.

In a preferred embodiment, the *Mycobacterium* for use in the vaccine compositions of the present invention is a Tokyo strain of BCG. In one embodiment, the *Mycobacterium* for use in the vaccine compositions of the present invention is BCG Tokyo 172 (ATCC 35737; TMC1019). The BCG Tokyo strain for use in the vaccine compositions provided herein can be the Type I or Type II subpopulations or a combination or mixture thereof. It should be noted that the two subpopulations differ in their colony morphologies with Type I being smooth and Type II being rough. Further, smooth colonies have a characteristic 22-bp deletion in Rv3405c of the region of difference (RD) 16 (type I), while rough colonies are complete in this region (type II). Additionally, the subpopulation types also differ in their lipid phenotypes, with phenolic glycolipid (PGL) and phthiocerol dimycocerosate (PDIM) being found only in type I. Given that PGL has been shown to suppress the host recognition of total lipids via Toll-like receptor 2, it may be antigenic and involved in host responses, acting as a cell wall component.

In one embodiment, the strain of BCG present in a vaccine composition as provided herein is a genetically engineered strain of BCG. The strain of BCG can be genetically engineered to improve or enhance immune system function such as, for example, T cell-mediated immunity. The strain of BCG can be genetically engineered to be equipped with the membrane-perforating listeriolysin (Hly) of *Listeria monocytogenes* as shown in Grode et al. Increased vaccine efficacy against tuberculosis of recombinant *Mycobacterium bovis* bacille Calmette-Guérin mutants that secrete listeriolysin, J. of Clinical Investigation, Vol. 115: 9, September 2005, which is herein incorporated by reference in its entirety.

In one embodiment, the *Mycobacterium* is non-pathogenic. The non-pathogenic *Mycobacterium* can be heat-killed. The non-pathogenic *Mycobacterium* can be selected from *M. vaccae, M. obuense, M. parafortuitum, M. aurum, M. indicus pranii, M. phlei* and combinations thereof. In one embodiment, the non-pathogenic *Mycobacterium* is a rough variant. In one embodiment, the non-pathogenic *Mycobacterium* is a smooth variant. In one embodiment, the methods provided herein comprise administering a composition comprising *M. vaccae*. Further to this embodiment, the *M. vaccae* can be heat-inactivated. Further still to this embodiment, the *M. vaccae* can be strain NCTC11659. Even further still to this embodiment, the composition comprising *M. vaccae* is SRL172. SRL172 is a suspension of heat-killed whole cell *Mycobacterium vaccae*. In one embodiment, the methods provided herein comprise administering a composition comprising *M. obuense*. Further to this embodiment, the *M. obuense* can be heat-inactivated. Further still to this embodiment, the *M. obuense* can be strain NCTC13365. Even further still to this embodiment, the composition comprising *M. obuense* is IMM-101. IMM-101 is a suspension of heat-killed whole cell *Mycobacterium obuense*.

In one embodiment, the compositions provided herein can be used as vaccines and can accordingly be formulated as pharmaceutical compositions.

In one embodiment, administration of any vaccine composition provided herein (e.g., a vaccine composition comprising an isolated *Mycobacterium* or antigenic fragment thereof) reduces, eliminates or alleviates one or more symptoms of FM. The one or more symptoms can be selected from chronic muscle pain, muscle spasms, or tightness, moderate or severe fatigue and decreased energy, insomnia or feeling of exhaustion, stiffness upon waking or after staying in one position for too long, difficulty remembering, concentrating, and performing simple mental tasks ("fibro fog"), abdominal pain, bloating, nausea, and constipation alternating with diarrhea (irritable bowel syndrome), tension or migraine headaches, jaw and facial tenderness, sensitivity to one or more of odors, noise, bright lights, medications, certain foods, and cold, feeling anxious or depressed, numbness or tingling in the face, arms, hands, legs, or feet, increase in urinary urgency or frequency (irritable bladder), reduced tolerance for exercise and muscle pain after exercise. a feeling of swelling (without actual swelling) in the hands and feet or a combination thereof. The reduction, elimination or alleviation can be as compared to a control. The control can be the individual prior to administration of the vaccine composition or a separate individual suffering from FM. In one embodiment, the reduction, elimination or alleviation of the one or more symptoms can be determined by evaluating the individual according to the Fibro-fatigue scale.

In another embodiment, administration of any vaccine composition provided herein (e.g., the vaccine composition comprising an isolated *Mycobacterium* or antigenic fragment thereof) increases immune system functioning. The increase in immune system functioning can be evidenced by the production or elevation thereof of $T_H1$ cytokines, upregulation of granzyme B or both. The $T_H1$ cytokines that are elevated or produced in response to administration of the compositions provided herein can include IFN-γ, IL-2, or TNF-β or a combination thereof. The increase immune system function can be evidenced by an elevation or increase in the production of one or more cytokines provided herein such as, for example, the cytokines listed in Table 1. Assessment of the alteration in immune function can be ascertained using the methods and/or kits provided herein and/or as described in US20150301062.

In one embodiment, administration of any vaccine composition provided herein (e.g., a vaccine composition comprising an isolated *Mycobacterium* or antigenic fragment thereof) to an individual suffering from or suspected of suffering from CFS reduces, eliminates or alleviates one or more symptoms of CFS. The one or more symptoms can be selected from a substantial reduction or impairment in the ability to engage in pre-illness levels of occupational, educational, social, or personal activities, post-exertional malaise, unrefreshing sleep, cognitive impairment, orthostatic intolerance, pain, gastrointestinal and genitourinary problems, sore or scratchy throat, painful or tender axillary/cervical lymph nodes, sensitivity to external stimuli, immune system problems, hormonal imbalances or any combination thereof. The reduction, elimination or alleviation can be as compared to a control. The control can be the individual prior to administration of the vaccine composition or a separate individual suffering from CFS. In one embodiment, the reduction, elimination or alleviation of the one or more symptoms can be determined by evaluating the individual according to the Fibro-fatigue scale.

In another embodiment, administration of any vaccine composition provided herein (e.g., the vaccine composition comprising an isolated *Mycobacterium* or antigenic fragment thereof) to an individual suffering from or suspected of suffering from CFS increases immune system functioning. The increase in immune system functioning can be evidenced by the production or elevation thereof of $T_H1$ cytokines, upregulation of granzyme B or both. The $T_H1$ cytokines that are elevated or produced in response to administration of the compositions provided herein can include IFN-γ, IL-2, or TNF-β or a combination thereof. The increase immune system function can be evidenced by an elevation or increase in the production of one or more cytokines provided herein such as, for example, the cytokines listed in Table 1. Assessment of the alteration in immune function can be ascertained using the methods and/or kits provided herein and/or as described in US20150301062.

Administration of Compositions

In certain embodiments, the compositions described herein (e.g., the immunogenic vaccine compositions) comprise, or are administered in combination with, an adjuvant. The adjuvant for administration in combination with a composition described herein may be administered before, concomitantly with, or after administration of said composition. In some embodiments, the term "adjuvant" can refer to a compound that when administered in conjunction with or as part of a composition described herein augments, enhances and/or boosts the immune response to an antigen present in the composition (e.g., the isolated *Mycobacterium* or antigenic fragment derived therefrom) but when the compound is administered alone does not generate an immune response to the antigen present in the composition (e.g., the isolated *Mycobacterium* or antigenic fragment derived therefrom). In some embodiments, the adjuvant generates an immune response to the antigen present in the composition (e.g., an isolated *Mycobacterium* or antigenic fragment derived therefrom) and does not produce an allergy or other adverse reaction. Adjuvants can enhance an immune response by several mechanisms including, e.g., lymphocyte recruitment, stimulation of B and/or T cells, and stimulation of macrophages. When a vaccine or immunogenic composition of the invention comprises adjuvants or is administered together with one or more adjuvants, the adjuvants that can be used include, but are not limited to, mineral salt adjuvants or mineral salt gel adjuvants, particulate adjuvants, microparticulate adjuvants, mucosal adjuvants, and immunostimulatory adjuvants. Examples of adjuvants for use in the methods and compositions provided herein can include, but are not limited to, cytokines (e.g., IL-12), heat-shock proteins, aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), ASO4 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)).

The compositions provided herein can comprise an antigen (e.g., an isolated *Mycobacterium* or antigenic fragment derived therefrom) alone or, preferably, together with a pharmaceutically acceptable carrier. Suspensions or dispersions of an antigen (e.g., an isolated *Mycobacterium* or antigenic fragments derived therefrom), especially isotonic aqueous suspensions or dispersions, can be used. The pharmaceutical compositions may be sterilized and/or may comprise excipients, e.g., preservatives, stabilizers, wetting agents and/or emulsifiers, solubilizers, salts for regulating osmotic pressure and/or buffers and are prepared in a manner known per se, for example by means of conventional dispersing and suspending processes. The said dispersions or suspensions may comprise viscosity-regulating agents. The suspensions or dispersions are kept at temperatures around 2-4° C., or preferentially for longer storage may be frozen and then thawed shortly before use. For injection, the vaccine or immunogenic preparations may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

In certain embodiments, the compositions described herein additionally comprise a preservative, e.g., the mercury derivative thimerosal. In a specific embodiment, the pharmaceutical compositions described herein comprises 0.001% to 0.01% thimerosal. In other embodiments, the pharmaceutical compositions described herein do not comprise a preservative.

The compositions of the invention may be administered to mammals (e.g., rodents, humans) in any suitable formulation. For example, isolated *Mycobacterium* or antigenic fragments thereof may be formulated in pharmaceutically acceptable carriers or diluents such as physiological saline or a buffered salt solution. Suitable carriers and diluents as provided herein can be selected on the basis of mode and route of administration and standard pharmaceutical practice.

The compositions of the invention may be administered to mammals by any conventional technique. Typically, such administration will be oral, sublingual, nasal, pulmonary or parenteral (e.g., intravenous, subcutaneous, intravesicular, intramuscular, intraperitoneal, intradermal, subdermal, or intrathecal introduction). The compositions may also be administered directly to a target site by, for example, surgical delivery to an internal or external target site, or by catheter to a site accessible by a blood vessel. The compositions may be administered in a single bolus, multiple injections, or by continuous infusion (e.g., intravenously, by peritoneal dialysis, pump infusion). For parenteral administration, the compositions are preferably formulated in a sterilized pyrogen-free form.

Dosing

The compositions (e.g., vaccine compositions) described above are preferably administered to a mammal (e.g., a human) in an effective amount, that is, an amount capable of producing a desirable result in a treated individual (e.g., activating or boosting the immune response). Such a therapeutically effective amount can be determined as described below.

Toxicity and therapeutic efficacy of the compositions utilized in methods of the invention can be determined by standard pharmaceutical procedures, using either cells in culture or experimental animals to determine the $LD_{50}$ (the dose lethal to 50% of the population). The dose ratio between toxic and therapeutic effects is the therapeutic index and it can be expressed as the ratio $LD_{50}/ED_{50}$. Those compositions that exhibit large therapeutic indices are preferred. While those that exhibit toxic side effects may be used, care should be taken to design a delivery system that minimizes the potential damage of such side effects. The dosage of preferred compositions lies preferably within a range that includes an $ED_{50}$ with little or no toxicity. The dosage may vary within this range depending upon the dosage form employed and the route of administration utilized.

As is well known in the medical and veterinary arts, dosage for any one subject depends on many factors, including the subject's size, body surface area, age, the particular composition to be administered, time and route of administration, general health, and other drugs being administered concurrently.

In certain embodiments, a particular dosage of a vaccine composition provided herein (e.g., vaccine comprising a strain of BCG) is administered to a subject. In certain embodiments of the invention, there is provided a vaccine composition comprising a live-attenuated or heat-killed bacteria (e.g., strain of BCG) for use in the present invention, which typically may be from $10^3$ to $10^{11}$ cells or colony forming units (CFUs), from $10^4$ to $10^{10}$ cells or CFUs, from $10^6$ to $10^{10}$ cells or CFUs, or $10^6$ to $10^9$ cells or CFUs per unit dose. The effective amount of live-attenuated or heat-killed *Mycobacterium* for use in the methods or compositions provided herein can be from $10^3$ to $10^{11}$ cells or CFUs, from $10^4$ to $10^{10}$ cells or CFUs, from $10^6$ to $10^{10}$ cells or CFUs, and from $10^6$ to $10^9$ cells or CFUs per unit dose. The unit dose can be 5 ul, 10 ul, 20 ul, 30 ul, 40 ul, 50 ul, 60 ul, 70 ul, 80 ul, 90 ul, 100 ul, 125 ul, 150 ul, 175 ul, 200 ul, 250 ul, 300 ul, 350 ul, 400 ul, 450 ul, 500 ul, 600 ul, 650 ul, 700 ul, 750 ul, 800 ul, 850 ul, 900 ul, 950 ul, 1000 ul or 1500 ul. In one embodiment, the vaccine comprises a therapeutically effective amount of live-attenuated or heat-killed *Mycobacterium* (e.g., strain of BCG such as Tokyo Strain) is from $1.8\times10^6$ to $3.9\times10^6$ colony forming units per unit dose, wherein the unit dose is 0.1 ml. Alternatively, the dose of a vaccine composition provided herein can be from 0.01 mg to 1 mg, 0.1 mg to 0.5 mg, 0.5 mg to 1 mg, 1 mg to 1.5 mg or 1.5 mg to 2.0 mg. In one embodiment, the dose is 1 mg. In one embodiment, the dose is 0.5 mg. In one embodiment, the dose is 0.1 mg. The organisms or antigenic fragments derived therefrom can be presented as either a suspension or dry preparation. Further to the above embodiments, the route of administration can be intradermal (ID) administration.

The composition may advantageously further comprise vitamin $B_{12}$ and/or folacin. It has been found that a subgroup of patients suffering from fibromyalgia or chronic fatigue syndrome, may also have levels of vitamin $B_{12}$ in their cerebrospinal fluid that are lower than normal, and levels of homocysteine that are higher than normal.

The composition according to the invention may also comprise, such as pharmaceutically acceptable additives, e.g. solvents, adjuvants, carriers and/or preservatives as provided herein.

The methods of treatment for FM, CFS and/or related conditions as provided herein can be conducted as a series of administrations with increasing doses during a specific period. In one example, the vaccine composition can be administered in 8-10 increasing doses during 4-12 weeks, preferably 8-10 weeks. The reason for the increasing doses can be that during the first week or weeks the patient may suffer from side effects, and it is therefore advantageously to start with a low dose. The side effects may diminish after some time. In one embodiment, the vaccine composition can be administered in 2 doses spaced 4 weeks apart.

In order to obtain the desired effect for a prolonged period of time the vaccine preparation (e.g., vaccine comprising BCG) may be administered at several occasions. For example, a first series of administrations may be followed by repeated administrations given at specified intervals. The specified intervals can be approximately once a week for 5-15 weeks, preferably for 10 weeks.

To prevent recurrence, the repeated administrations may then be followed by a maintenance treatment with administrations at specified intervals. The specified intervals can be approximately once a month. The specified intervals may be continued for several years, such as 1-10 years, or approximately 5 years. In one embodiment, the maintenance treatment entails one injection of the vaccine composition per year for a specified interval of 4 years.

The doses in the repeated administrations of the maintenance treatment can be constant. In some cases, the doses in the maintenance treatment can be the dose used in the last administration in the first series.

These repeated administrations can result in an unspecific or specific activation of the immune system over a long period of time.

The administrations can be made in any way known in the art, such as, for example, injections.

Additional agents or substances can be administered simultaneously or in parallel with the vaccine compositions of the present invention. The additional agents or substance can be, for example, vitamin B12 and/or folacin.

Assessing Treatment Efficacy

In another aspect, the invention provides methods for evaluating the efficacy of treatment in an individual diagnosed with FM or CFS. In one embodiment, the method for evaluating treatment efficacy in an individual diagnosed with FM entails subjecting the individual to the FibroFatigue scale following treatment or at various points during treatment. In one embodiment, the method for evaluating treatment efficacy in an individual diagnosed with CFS entails evaluating the individual diagnosed with CFS, following treatment or at various points during treatment, for improvements in the set of symptoms used to make the CFS diagnosis such as, for example, evaluating any improvement in activities of daily living and/or improvements in physical and mental functioning. Alone or in combination with the previous two embodiments, the method for evaluating the efficacy of treatment in an individual diagnosed with FM or CFS involves determining or detecting as a baseline the level of one or more cytokines expressed in the individual diagnosed with or suspecting of having FM or CFS prior to treatment. Following treatment (e.g., vaccination), subsequent measurements of one or more cytokine levels are carried out to determine the levels or patterns of expression of the one or more cytokines. The altered levels and/or patterns of expression of one or more of the cytokines measured in the individual afflicted with FM or CFS or at risk for developing FM or CFS and undergoing treatment are compared to the levels or patterns of expression of cytokines in a control. In one embodiment, the control is the levels and/or patterns of expression of the one or more cytokines in the individual before treatment. In another embodiment, the control is the levels and/or expression levels of the one or more cytokines from a healthy patient, or cytokine levels reported for a patient without fibromyalgia or CFS (for example, levels reported in a database).

In one embodiment, the methods for assessing treatment efficacy involve determining or assaying the levels of at least one, at least two, at least three, at least four, at least five, at least six, at least seven, at least eight, at least nine, or at least ten or more cytokines in the plasma of blood samples obtained from individuals suspected of being afflicted with FM or CFS or at risk for FM or CFS after treatment with the compositions (e.g., the compositions comprising isolated *Mycobacterium* or antigenic fragments thereof) and comparing the levels of the assayed cytokines to a control. The control can be any control as provided herein. In a further embodiment, the method involves determining or assaying the levels of at least one, at least two, at least three, at least four, at least five, at least six, at least seven, at least eight, at least nine, or at least ten or more cytokines in the peripheral blood mononuclear cells (PBMCs) that have been separated from the plasma of blood samples obtained from the individuals after treatment and comparing the levels of the assayed cytokines to a control. The control can be any control as provided herein. These levels are then analyzed to determine if the levels are altered due to the treatment. For example, the levels in the individual's sample during and/or after treatment, in one embodiment, are compared to levels in a control sample, for example, a sample known to not have FM or CFS. In another embodiment, control levels are known, for example, from a database. In one embodiment, a change in expression in a majority of the cytokines tested toward the levels in the control is determinative/indicative of the treatment for FM or CFS being efficacious. In another embodiment, a change in expression of at least about 33% or at least about 67% of the cytokines tested is determinative/indicative of an effective treatment for FM or CFS. In a further embodiment, a treatment with a composition as provided herein is deemed to be efficacious for treating fibromyalgia or CFS if at least about 75%, or at least about 75% or more of the cytokines tested have altered expression due to the treatment. In even a further embodiment, a treatment with a composition as provided herein is deemed to be efficacious for treating fibromyalgia or CFS if the expression level of every cytokine tested, or about every cytokine tested in the patient is altered. The altered expression of one or more cytokines during or following treatment can be modifying the level or expression of the one or more cytokines to be substantially the same expression level of the one or more cytokines in a control (e.g., the levels in a healthy patient who does not have FM or CFS). As used herein, the term "substantially the same expression level" can be about 55%, about 60%, about 65%, about 70%, about 75%, about 80%, about 85%, about 90%, about 95%, about 99% or about 99% of the expression level of a particular cytokine in a control as provided herein.

The present invention is not limited by any particular combination of cytokines. For example, the cytokines to whose expression can be evaluated in order to determine treatment efficacy can be selected from IL-1, IL-2, IL-4, IL-5, IL-6, IL-7, IL-8, IL-10, IL-12, IL-13, IL-15, IL-17, IL-21, IFN-γ, IFN-α, TNF-α, IP-10, MCP-1, MIG, MIP-1α, MIP-1β, GM-CSF, Eotaxin, RANTES, etc. or a combination thereof. In another aspect, the invention further includes determining the levels of one or more of IL-1RA, IL2R, IL-7, IL-12 (p40/p70), IL-13, IL-15, IL-17, IFN-α, IP-10, MIG, VEGF, G-CSF, EGF, granzyme B, FGF-basic and HGF or a combination thereof. In yet another aspect, the invention also includes determining the levels of IL-9 and PDGF-BB or a combination thereof. The cytokine may be inflammatory or anti-inflammatory. In one embodiment, the cytokine to be assayed may be a full length polypeptide, protein, a glycoprotein or a fragment thereof. Other proteins that can be assayed include hormones, heat-shock proteins, antibodies such as but not limited to anti-nuclear antibody (ANA), thyroid antibodies, anti-extractable nuclear antibodies (ENA), IgG subclasses, anti-nuclear factors (FAN), rheumatoid factor (RF), receptor proteins and ligands, etc. In other embodiment, the level of cytokine assayed maybe a mRNA, miRNA, or DNA. In another example, the expression levels of cytokines included in commercial cytokine panels (or cytokine subsets thereof) can be evaluated by the methods provided herein. Various combinations of cytokines for use in the present invention are provided in the Table 1 as provided herein. Subsets of these combinations may also be used in the methods provided herein. It should be understood that these combinations are representative, and should not be construed as limiting the invention.

Measurement/Detection of Cytokine Levels

In one embodiment, cytokine levels in methods entailing diagnosing and/or assessing treatment efficacy as provided herein are tested on the protein level. In another embodiment, cytokine levels in methods entailing diagnosing and/or assessing treatment efficacy as provided herein are determined at the mRNA level. In yet another embodiment, both mRNA and protein levels for the cytokines are examined in the methods provided herein. Methods for assaying cytokines at the protein or mRNA levels are well known in the art and can be employed in the methods provided herein.

Measuring cytokine levels in methods entailing diagnosing and/or assessing treatment efficacy as provided herein can be from blood or a plasma sample that may be stimulated or un-stimulated. That is, cell proliferation may be induced prior to assaying the cytokine levels. In one embodiment, the PBMCs are un-stimulated. In another embodiment, the PBMCs are stimulated to cause proliferation of the cells prior to assaying for cytokines. Methods for stimulating PBMCs are known in the art, and include, but are not limited to, the addition of mitogens to the cells. Non-limiting examples of mitogens include lipopolysaccharide (LPS), phytohemagglutinin (PHA), or phorbol ester, such as phorbol myristate acetate (PMA) with or without ionomycin, pokeweed mitogen (PWM), concavalin A (Con-A), or combinations thereof.

In one embodiment, cytokine expression is measured at the mRNA level, for example, by quantitative RT-PCR (also known as real time RT-PCR). mRNA expression levels can also be measured by Northern blot assay, array hybridization, sequencing, etc. For example, multiplex quantitative RT-PCR, in one embodiment, is carried out to determine the mRNA expression levels of a cytokine panel. Cytokine RT-PCR kits are commercially available, for example, from Roche.

In another embodiment, secreted cytokine levels are determined (i.e., at the protein level). In one embodiment, secreted cytokine levels are determined by using an antibody array, for example, the TranSignal Human Cytokine Antibody Array 3.0, available from Panomics. The Panomics array includes antibodies directed to the following cytokines: Apol/Fas, Leptin, Rantes, ICAM-1, IL-2, IL-7, CTLA, MIP-1α, MIP-1β, TGFβ, VCAM-1, IL-3, IL-8, IL-4, IL-10, IL-5, IL-12, IL-6, IL-15, IL-6R, IL-17, IL-1Rα, IL-1β, IL-1α, VEGF, IFNγ, TNFα, TNFRI, TNFRII, MIP-5, MIP-4, MMP3, Eotaxin, GM-CSF, EGF, IP-10. In this embodiment, not all cytokines in the array need be probed for. For example, the expression levels of a subset of five cytokines, or five or more cytokines, or six cytokines, or six or more cytokines, or seven cytokines, or seven or more cytokines, or ten cytokines, or ten or more cytokines, or twelve cytokines, or twelve or more cytokines may be determined when carrying out the methods of the invention.

Secreted cytokine levels, in one embodiment, are determined with a multiplex immunoassay built on magnetic beads. For example, in one embodiment, the Bio-Plex Pro magnetic Cytokine Assay is used (Bio-Rad). In this embodiment, the Assay is commercially available as a ready to use kit, for example, for the detection of eight cytokines, seventeen cytokines, 21 cytokines or 27 cytokines. The full number or a subset of the cytokines may be detected in the methods of the invention. Alternatively, expression levels of cytokines can be tested in a sample by doing multiple assays on the sample, for example, in "singleplex" format. In one embodiment, the Bio-Rad singleplex cytokine assays are used.

Another antibody based bead assay is available from Invitrogen, and is also amenable to be used in the methods of the present invention. Specifically, the Human Cytokine Thirty-Plex antibody bead kit may be employed to detect the levels of a panel of cytokines in an individual. Although the assay can detect the levels of thirty cytokines, not all thirty need to be detected in order to carry out the methods provided herein. For example, as provided above, five, six, seven, eight, nine, ten, eleven or twelve cytokines can be assayed for their expression levels. The Invitrogen kit comprises analyte specific components for the measurement of human IL-1β, IL-1RA, IL-2, IL-2R, IL-4, IL-5, IL-6, IL-7, IL-8, IL-10, IL-12p40/p70, IL-13, IL-15, IL-17, TNF-α, IFN-α, IFN-γ, GM-CSF, MIP-1α, MIP-1β, IP-10, MIG, Eotaxin, RANTES, MCP-1, VEGF, G-CSF, EGF, FGF-basic, and HGF. These reagents, in one embodiment, are used in the Luminex® 100™ or 200™ System.

Methods for assaying cytokines at the protein or mRNA levels are well known in the art. Besides the assays provided above, other non-limiting examples of methods for assaying cytokines at the protein level include enzyme-linked immunoassay (ELISA), Tetramer assay, ELISPOT assay, Fluorospot assay, etc. The cytokines concentration in the plasma, culture supernatant, or cell lysate derived from PBMC can be measured, for example, by multiplex immunoassay based on Luminex xMAP bead array technology, or Bio-Plex 200 fluorescence bead reader (BioRad Laboratories, Hercules, Calif.). In one embodiment, the level of one or more cytokine mRNA can be detected (measured) by real time PCR, RT-PCR, Northern blot assay, array hybridization, sequencing, etc. The altered level(s) of the cytokines measured in the affected individual compared to the level from control group is predictive/indicative of FM in the individual. The cytokine levels in an individual with FM, for example, cytokine levels in a FM patient's blood, in one embodiment, are higher than the cytokine levels of a healthy patient, for each cytokine tested. In another embodiment, the cytokine levels in a FM patient's blood are lower than the cytokine levels of a healthy patient, for each cytokine tested. In yet another embodiment, the cytokine levels measured in a patient with FM may be higher or lower, depending on the panel of cytokines measured in the individual.

The level of cytokines can be determined using an algorithm and the raw data obtained by measuring the levels of cytokines which have been stored in a computer system, or any other medium that is linked to a computer or machine. In one aspect, the method further includes evaluation of the individual's (i.e., individuals diagnosed with FM or CFS) clinical and physical symptoms as described herein in conjunction with determining the levels of one or more cytokines. For example, in an individual diagnosed with FM, the method can include evaluation of physical and mental functioning as well as tender points in the individual. The physical and mental functioning as well as the pain threshold can be calculated and assigned a score on a subjective basis. In another example, in an individual diagnosed with CFS, the method can involve evaluation of the set of symptoms used to make the original diagnosis such as, for example, evaluating the individual's daily activity and/or physical and mental functioning. The level of daily activity as well as the physical and mental functioning can be calculated and assigned a score on a subjective basis. The scores derived from the assessment of the clinical and physical symptoms may be included in the statistical analysis for the cytokines. In a further embodiment, the method includes determining the levels of various factors or markers, such as but not limited to Rheumatoid Factor (RF), or a specific marker of inflammation such as the erythrocyte sedimentation rate (ESR).

As it relates to the diagnostic and/or assessment of treatment efficacy methods provided herein, cytokine expression can be "altered" or "differentially expressed", in an individual, in one embodiment, if expression of the cytokine in the individual's sample is at least about 1.5 times higher or lower than the expression of the same cytokine at a control level. In another embodiment, cytokine expression is "altered" if cytokine expression in the individual's sample is at least about 2 times higher or lower than the expression of the same cytokine at a control or baseline level (i.e., levels reported for a healthy patient). In another embodiment, cytokine expression is "altered" if cytokine expression in the individual is at least about 2.5 times higher or lower (or at least about 2.5 times or more higher or lower) than the control expression level of the same cytokine. In yet another embodiment, cytokine expression is "altered" if cytokine expression in the individual is at least about 3 times higher or lower (or at least about 3 times or more higher or lower) than the control expression level of the same cytokine. In another embodiment, cytokine expression is "altered" if cytokine expression in the individual is at least about 5 times higher or lower (or at least about 5 times or more higher or lower) than the control expression level of the same cytokine. In even another embodiment, cytokine expression is "altered" if cytokine expression in the individual is at least about 10 times higher or lower than the control expression level of the same cytokine in a control sample. In yet another embodiment, cytokine expression is altered if cytokine expression in the individual is at least about 10 times or more, higher or lower, than the control expression level of the same cytokine. As provided above, control expression level may be determined from values in a database, from a non-disease sample (e.g., FM or CFS) or individual.

Altered expression of the cytokine may be the same or different for each individual cytokine that is differentially expressed. For example, the expression of one cytokine (mRNA or protein) may be 2× lower, or about 2× lower, than the expression of the same cytokine in a control sample, while the expression of a second cytokine may be 1.5× lower, or about 1.5× lower, than the expression of the same cytokine in a control sample. As discussed above, altered expression includes both higher and lower expression of the cytokine, compared to a control level.

EXAMPLES

Example 1

A Placebo-Controlled Study to Evaluate the Safety and Efficacy of *Mycobacterium* Vaccines in Treating Fibromyalgia (FM)

The primary objective of this study will be to evaluate the efficacy of two heat-killed whole cell *Mycobacterium* compositions for boosting the immune system of patients suffering from fibromyalgia (FM). Secondary objectives will be to evaluate the safety and tolerability of both of the *Mycobacterium* compositions as well as investigate local injection site reactions.

Study Patients and Dosing Schedule

The study will be in the form of a prospective, randomized, double-blind, placebo-controlled, parallel-group study using different *Mycobacterium* comprising compositions. Male and female patients (over 18 years) who have a positive FM/a® score as assessed using the FM/a® fibromyalgia blood test are included in this trial. The main exclusion criteria will include pregnant and lactating woman, patients suffering from other inflammatory rheumatological diseases (such as rheumatoid arthritis or collagenoses), severe neuropathies, clinically manifest endocrinopathies, bone diseases, severe cardial, renal or hepatic impairment and acute or chronic infections.

75 Patients will be randomly assigned to one of three study cohorts: placebo (25 patients; cohort 1), IMM-101 (*M. obuense* composition; 25 patients; cohort 2) or SRL172 (*M. vaccae* composition; 25 patients; cohort 3). The duration of treatment will be four weeks over which each patient will receive (3) intradermal (i.d.) injections. Each dose will be administered in each patient from one of the three cohorts into the skin overlying the deltoid muscle with the arm alternated for each dose. Prior to commencement of the study, each patient in each cohort will receive a placebo injection of borate saline solution (day −3) to provide an intra-patient placebo control and to allow the patient to practice completion of the diary and assess whether patients are capable of measuring their own in injection site reactions accurately. Patients who are willing and able to proceed with the study will be injected with a single dose level of placebo (borate saline-solution, cohort 1); IMM-101 (cohort 2) or SRL172 (cohort 3) on (3) subsequent occasions. Doses of placebo, IMM-101 or SRL172 will be administered over a 4-week period on days 0, 14 and 28 (with up to 2 days variation in the dosing interval). For cohort 1, a standard volume of 0.1 ml of borate saline-solution will be injected. For cohort 2, a standard volume of 0.1 ml of a suspension containing *M. obuense* at the concentration of 10 mg/ml will be injected. For cohort 3, a standard volume of 0.1 ml of a suspension containing $10^9$ bacilli of *M. vaccae* will be injected.

Before, on each dosing day and at the end of the treatment phase (i.e., at screening and at days 3, 14, 28 and 42), routine safety assessments will be performed using physical examinations, urinalysis, electrocardiograms and hematological and biochemical blood tests. Further, at days 0, 3, 14, 28 and 42, local tolerability will be assessed using standardized techniques (measurements at injection site) by a study physician or research nurse and the intensity of each injection site reaction will be scored with reference to a Vaccine Toxicology Rating Scale (available at *Annals of Oncology* online). Additionally, at screening and at days 3, 14, 28 and 42, a pain assessment and blood testing for cytokine levels will be performed in order to assess physical signs and symptoms of FM as well as the biochemical effects of the vaccination protocol, respectively.

In order to document daily the intensity of pain, adverse events and concomitant medications, patients will use a standardized diary and will record daily the parameters mentioned. In addition, changes in functional symptoms will be documented at start of treatment, as well as on day 3, day 14, day 28 and at the end of treatment (day 42). Adverse events will be assessed during the active treatment period.

To evaluate pain, the pain score, a visual analogue scale and clinical examination of tender points will be used. The pain score ranges from 0 to 120, measuring the pain intensity in 24 body regions applied to the following rating scale: 0=no pain, 1=mild pain, 2=moderate pain, 3=moderately severe pain, 4=severe pain, 5=most ever pain. The assessment of each body region will be done by the patients themselves; the total score will be calculated as the sum of the regional scores.

The visual analogue scale is in the form of 100-mm-line oriented horizontally with one end=0, indicating "no pain" and the other end=100, indicating "worst pain". The patients are asked to place a mark corresponding to their perception of their present pain intensity.

In addition to the documented effects during the active treatment phase, a follow-up of the patients will be performed for six months in order to evaluate the duration of the clinical response (as defined by a 35% or higher reduction in individual pain score/baseline versus end of treatment).

Cytokine Assay

In order to measure cytokine levels (i.e., IL-2 and IFN-gamma), at screening and at days 3, 14, 28 and 42, twenty-30 mL of blood will be drawn from each patient from each cohort in 7-mL tubes containing 0.081 mL of 15% $K_3$-EDTA solution (BD Vacutainer®, BD, Franklin Lakes, N.J.) by venipuncture. Blood will be transferred to 50-mL tubes and diluted 1:1 in GIBCO® Hank's balanced salt solution (HBSS, Invitrogen, Carlsbad, Calif.). The resulting solution will be layered on top of 15 mL Ficoll (Histopaque-1077, Sigma-Aldrich, St. Louis, Mo.) in 50-mL tubes and centrifuged at 1800 rpm for 20 minutes. The top layer will aspirated and discarded and the interphase containing PMBC will be harvested and transferred into a new 50-mL tube. The tube will be filled with HBSS and the contents mixed by gentle rocking. Cells will be collected by centrifugation at 2000 rpm for 10 minutes and resuspended in 10 mL complete RPMI-1640 medium supplemented with 10% fetal bovine serum, 1% penicillin-streptomycin mixture and 1% L-glutamine solution (Invitrogen, Carlsbad, Calif.). Cell viability and count will be determined using Trypan blue exclusion assay.

Cytokine and chemokine concentrations in plasma will be measured by multiplex immunoassay based on Luminex xMAP™ bead array technology and Bio-Plex 200 fluorescence bead reader (BioRad Laboratories, Hercules, Calif.). Three panels of antibody-conjugated beads for measuring human inflammatory cytokines (GM-CSF, IL-1β, IL-6, IL-8, TNF-α), Th1/Th2 cytokines (IFN-γ, IL-2, IL-4, IL-5, IL-10) and chemokines (MIP-1α, MIP-1β, MCP-1, Eotaxin, RANTES) (BioSource, Camarillo, Calif.) will be used in the assay according to the manufacturer instructions. Other panels that can be included are IL-1RA, IL-2R, IL-7, IL-12 (p40/p70), IL-13, IL-15, IL-17, IFN-, IP-10, MIG, VEGF, EGF, FGF-basic, and HGF (InVitrogen) or IL-IRA, IL-7, IL-9, IL-12, IL13, IL-15, IL-17, FGF-basic, G-CSF, IP-10, VEGF, PDGF-BB (BioRad)

Concentration values will be transferred to Microsoft Office Excel 2003 software (Microsoft Corporation, Redmond, Wash.) and means as well as standard deviations will be calculated for each cytokine concentration. Cytokine concentrations in patients from cohorts 2 and 3 will be compared to those of cohort 1 by using Student's t-test. The confidence level will be set at 5%. In addition, analysis of a potential correlation between cytokine induction (i.e., IL-2 and/or IFN-gamma) and modification of physical/function FM signs & symptoms will be performed using software and statistical analyses.

Example 2

A Placebo-Controlled Study to Evaluate the Safety and Efficacy of a BCG Vaccine in Treating Fibromyalgia (FM)

The primary objective of this study will be to evaluate the efficacy of a BCG vaccine for boosting the immune system of patients suffering from fibromyalgia (FM). Secondary objectives will be to evaluate the safety and tolerability of both of the BCG vaccine as well as investigate local injection site reactions.

Study Patients and Dosing Schedule

The study will be in the form of a prospective, randomized, double-blind, placebo-controlled, parallel-group study using a BCG vaccine. Male and female patients (over 18 years) who have a positive FM/a® score as assessed using the FM/a® fibromyalgia blood test are included in this trial. The main exclusion criteria will include pregnant and lactating woman, patients suffering from other inflammatory rheumatological diseases (such as rheumatoid arthritis or collagenoses), severe neuropathies, clinically manifest endocrinopathies, bone diseases, severe cardial, renal or hepatic impairment and acute or chronic infections.

50 Patients will be randomly assigned to one of two study cohorts: placebo (25 patients; cohort 1) or BCG vaccine (25 patients; cohort 2). The BCG used will be Tokyo BCG (JBL, Tokyo, Japan). The duration of treatment will be four weeks over which each patient will receive (2) intradermal (ID) injections. Each dose will be administered in each patient from one of the two cohorts into the skin overlying the deltoid muscle with the arm alternated for each dose. Prior to commencement of the study, each patient in each cohort will receive a placebo injection of borate saline solution (day −3) to provide an intra-patient placebo control and to allow the patient to practice completion of the diary and assess whether patients are capable of measuring their own in injection site reactions accurately. Patients who are willing and able to proceed with the study will be injected with a single dose level of placebo (borate saline-solution, cohort 1) or BCG (cohort 2) on (2) subsequent occasions. Doses of placebo or BCG will be administered over a 4-week period on days 0 and 28 (with up to 2 days variation in the dosing interval). For cohort 1, a standard volume of 0.1 ml of borate saline-solution will be injected. For cohort 2, a standard volume of 0.1 ml of a suspension containing BCG at the concentration of 1.8 to $3.9\times10^6$ cfu will be injected. All injections will be administered using a Biojector® B2000 device for intradermal (ID) administration.

Before, on each dosing day and at the end of the treatment phase (i.e., at screening and at days 3, 14, 28 and 42), routine safety assessments will be performed using physical examinations, urinalysis, electrocardiograms and hematological and biochemical blood tests. Further, at days 0, 3, 14, 28 and 42, local tolerability will be assessed using standardized techniques (measurements at injection site) by a study physician or research nurse and the intensity of each injection site reaction will be scored with reference to a Vaccine Toxicology Rating Scale (available at *Annals of Oncology* online). Additionally, at screening and at days 3, 14, 28 and 42, a pain assessment and blood testing for cytokine levels will be performed in order to assess physical signs and symptoms of FM as well as the biochemical effects of the vaccination protocol, respectively.

In order to document daily the intensity of pain, adverse events and concomitant medications, patients will use a standardized diary and will record daily the parameters mentioned. In addition, changes in functional symptoms will be documented at start of treatment, as well as on day 3, day 14, day 28 and at the end of treatment (day 42). Adverse events will be assessed during the active treatment period.

To evaluate pain, the pain score, a visual analogue scale and clinical examination of tender points will be used. The pain score ranges from 0 to 120, measuring the pain intensity in 24 body regions applied to the following rating scale: 0=no pain, 1=mild pain, 2=moderate pain, 3=moderately severe pain, 4=severe pain, 5=most ever pain. The assessment of each body region will be done by the patients themselves; the total score will be calculated as the sum of the regional scores.

The visual analogue scale is in the form of 100-mm-line oriented horizontally with one end=0, indicating "no pain" and the other end=100, indicating "worst pain". The patients are asked to place a mark corresponding to their perception of their present pain intensity.

In addition to the documented effects during the active treatment phase, a follow-up of the patients will be performed for six months in order to evaluate the duration of the clinical response (as defined by a 35% or higher reduction in individual pain score/baseline versus end of treatment).

Cytokine Assay

In order to measure cytokine levels (i.e., IL-2 and IFN-gamma), at screening and at days 3, 14, 28 and 42, twenty-30 mL of blood will be drawn from each patient from each cohort in 7-mL tubes containing 0.081 mL of 15% $K_3$-EDTA solution (BD Vacutainer®, BD, Franklin Lakes, N.J.) by venipuncture. Blood will be transferred to 50-mL tubes and diluted 1:1 in GIBCO® Hank's balanced salt solution (HBSS, Invitrogen, Carlsbad, Calif.). The resulting solution will be layered on top of 15 mL Ficoll (Histopaque®-1077, Sigma-Aldrich, St. Louis, Mo.) in 50-mL tubes and centrifuged at 1800 rpm for 20 minutes. The top layer will aspirated and discarded and the interphase containing PMBC will be harvested and transferred into a new 50-mL tube. The tube will be filled with HBSS and the contents mixed by gentle rocking. Cells will be collected by centrifugation at 2000 rpm for 10 minutes and resuspended in 10 mL complete RPMI-1640 medium supplemented with 10% fetal bovine serum, 1% penicillin-streptomycin mixture and 1% L-glutamine solution (Invitrogen, Carlsbad, Calif.). Cell viability and count will be determined using Trypan blue exclusion assay.

Cytokine and chemokine concentrations in plasma will be measured by multiplex immunoassay based on Luminex xMAP™ bead array technology and Bio-Plex 200 fluorescence bead reader (BioRad Laboratories, Hercules, Calif.). Three panels of antibody-conjugated beads for measuring human inflammatory cytokines (GM-CSF, IL-1β, IL-6, IL-8, TNF-α), Th1/Th2 cytokines (IFN-γ, IL-2, IL-4, IL-5, IL-10) and chemokines (MIP-1α, MIP-1β, MCP-1, Eotaxin, RANTES) (BioSource, Camarillo, Calif.) will be used in the assay according to the manufacturer instructions. Other panels that can be included are IL-1RA, IL-2R, IL-7, IL-12 (p40/p70), IL-13, IL-15, IL-17, IFN-, IP-10, MIG, VEGF, EGF, FGF-basic, and HGF (InVitrogen) or IL-IRA, IL-7, IL-9, IL-12, IL13, IL-15, IL-17, FGF-basic, G-CSF, IP-10, VEGF, PDGF-BB (BioRad).

Concentration values will be transferred to Microsoft Office Excel 2003 software (Microsoft Corporation, Redmond, Wash.) and means as well as standard deviations will be calculated for each cytokine concentration. Cytokine concentrations in patients from cohorts 2 and 3 will be compared to those of cohort 1 by using Student's t-test. The confidence level will be set at 5%. In addition, analysis of a potential correlation between cytokine induction (i.e., IL-2 and/or IFN-gamma) and modification of physical/function FM signs & symptoms will be performed using software and statistical analyses.

Example 3

A Placebo-Controlled Study to Evaluate the Safety and Efficacy of a BCG Vaccine in Treating Chronic Fatigue Syndrome (CFS)

The primary objective of this study will be to evaluate the efficacy of a BCG vaccine for boosting the immune system of patients suffering from CFS. Secondary objectives will be to evaluate the safety and tolerability of both of the BCG vaccine as well as investigate local injection site reactions.

Study Patients and Dosing Schedule

The study will be in the form of a prospective, randomized, double-blind, placebo-controlled, parallel-group study using a BCG vaccine. Male and female patients (over 18 years) who have been previously diagnosed with CFS are included in this trial. The main exclusion criteria will include pregnant and lactating woman, patients suffering from other inflammatory rheumatological diseases (such as rheumatoid arthritis or collagenoses), severe neuropathies, clinically manifest endocrinopathies, bone diseases, severe cardial, renal or hepatic impairment and acute or chronic infections.

50 Patients will be randomly assigned to one of two study cohorts: placebo (25 patients; cohort 1) or BCG vaccine (25 patients; cohort 2). The duration of treatment will be four weeks over which each patient will receive (3) intradermal (i.d.) injections. Each dose will be administered in each patient from one of the two cohorts into the skin overlying the deltoid muscle with the arm alternated for each dose. Prior to commencement of the study, each patient in each cohort will receive a placebo injection of borate saline solution (day −3) to provide an intra-patient placebo control and to allow the patient to practice completion of the diary and assess whether patients are capable of measuring their own in injection site reactions accurately. Patients who are willing and able to proceed with the study will be injected with a single dose level of placebo (borate saline-solution, cohort 1) or BCG (cohort 2) on (3) subsequent occasions. Doses of placebo or BCG will be administered over a 4-week period on days 0, 14 and 28 (with up to 2 days variation in the dosing interval). For cohort 1, a standard volume of 0.1 ml of borate saline-solution will be injected. For cohort 2, a standard volume of 0.1 ml of a suspension containing BCG at the concentration of 10 mg/ml will be injected.

Before, on each dosing day and at the end of the treatment phase (i.e., at screening and at days 3, 14, 28 and 42), routine safety assessments will be performed using physical examinations, urinalysis, electrocardiograms and hematological and biochemical blood tests. Further, at days 0, 3, 14, 28 and 42, local tolerability will be assessed using standardized techniques (measurements at injection site) by a study physician or research nurse and the intensity of each injection site reaction will be scored with reference to a Vaccine Toxicology Rating Scale (available at *Annals of Oncology* online). Additionally, at screening and at days 3, 14, 28 and 42, a physical examination, a pain assessment and full medical write-up will be performed in order to assess physical signs and symptoms of CFS as well as the biochemical effects of the vaccination protocol, respectively.

In order to document daily the intensity of pain, adverse events and concomitant medications, patients will use a standardized diary and will record daily the parameters mentioned. In addition, changes in functional symptoms will be documented at start of treatment, as well as on day 3, day 14, day 28 and at the end of treatment (day 42). Adverse events will be assessed during the active treatment period.

To evaluate pain, the pain score, a visual analogue scale and clinical examination of tender points will be used. The pain score ranges from 0 to 120, measuring the pain intensity in 24 body regions applied to the following rating scale: 0=no pain, 1=mild pain, 2=moderate pain, 3=moderately severe pain, 4=severe pain, 5=most ever pain. The assessment of each body region will be done by the patients themselves; the total score will be calculated as the sum of the regional scores.

The visual analogue scale is in the form of 100-mm-line oriented horizontally with one end=0, indicating "no pain" and the other end=100, indicating "worst pain". The patients are asked to place a mark corresponding to their perception of their present pain intensity.

In addition to the documented effects during the active treatment phase, a follow-up of the patients will be performed for six months in order to evaluate the duration of the clinical response (as defined by a 35% or higher reduction in individual pain score/baseline versus end of treatment).

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

All publications, patents and patent applications herein are incorporated by reference to the same extent as if each individual publication or patent application was specifically and individually indicated to be incorporated by reference. It is not an admission that any of the information provided herein is prior art or relevant to the presently claimed inventions, or that any publication specifically or implicitly referenced is prior art.

While the invention has been described in connection with specific embodiments thereof, the foregoing description has been given for clearness of understanding only and no unnecessary limitations should be understood therefrom. It will be understood that the description is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims. Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating fibromyalgia (FM) in a subject, comprising:

(a) determining dysfunction in peripheral blood mononuclear cells (PBMCs), wherein the determining the dysfunction comprises:

(i) stimulating a sample comprising PBMCs obtained from a subject; and (ii) measuring expression levels of at least four cytokines selected from the group consisting of IL-2, IL-4, IL5, IL6, IL8, IL 10, IFN-γ, RANTES, MCP-1, MIP-α and MIP-β in a PBMC sample obtained from the subject;

(b) comparing the expression levels of the at least four cytokines in the PBMC sample obtained from the subject to the expression levels of the at least four cytokines in a control sample of PBMCs;

(c) diagnosing the subject with FM if dysfunction in PBMCs is detected in the PBMCs obtained from the subject, wherein the dysfunction is indicated by altered expression levels of the at least four cytokines in the PBMC sample obtained from the subject as compared to the expression levels of the at least four cytokines in the control PBMC sample; and (d) administering a therapeutically effective amount of a vaccine to the subject diagnosed with FM, wherein the vaccine is a live-attenuated or heat-killed *Mycobacterium*, wherein the *Mycobacterium* is *Mycobacterium bovis* (*M. bovis*), *Mycobacterium vaccae* (*M. vaccae*) or *Mycobacterium obuense* (*M. obuense*).

2. The method of claim 1, wherein the vaccine induces one or more epigenetic changes in the genome of the subject.

3. The method of claim 1, wherein the administration of the vaccine alleviates, prevents or reduces at least one sign or symptom of fibromyalgia, wherein the sign or symptom is selected from chronic muscle pain, muscle spasms, muscle tightness, moderate or severe fatigue, decreased energy, insomnia, feeling of exhaustion, stiffness upon waking, stiffness after staying in one position for too long, difficulty remembering, difficulty concentrating, difficulty performing simple mental tasks ("fibro fog"), abdominal pain, bloating, nausea, constipation alternating with diarrhea (irritable bowel syndrome), tension or migraine headaches, jaw and facial tenderness, sensitivity to one or more of odors, noise, bright lights, medications, certain foods, and cold, feeling anxious or depressed, numbness or tingling in the face, arms, hands, legs, or feet, increase in urinary urgency or frequency (irritable bladder), reduced tolerance for exercise and muscle pain after exercise, a feeling of swelling (without actual swelling) in the hands and feet or any combination of symptoms thereof.

4. The method of claim 1, wherein the administration of the vaccine elevates or increases immune system activity of the subject.

5. The method of claim 4, wherein the elevation or increase in immune system function is evidenced by the production of TH1 cytokines, upregulation of granzyme B or both.

6. The method of claim 1, wherein the PBMCs are isolated from plasma of a blood sample obtained from the subject.

7. The method of claim 1, wherein the PBMCs are stimulated with one or more mitogens.

8. The method of claim 1, wherein the determined expression level for each of the at least four cytokines is a protein expression level, wherein the protein expression level is determined using an antibody bead-based capture assay that comprises beads derivatized with antibodies specific to the at least four cytokines.

9. The method of claim 1, wherein the *Mycobacterium* is *M. obuense.*

10. The method of claim 1, wherein the *Mycobacterium* is *M. vaccae.*

* * * * *

UNITED STATES PATENT AND TRADEMARK OFFICE

CERTIFICATE OF CORRECTION

PATENT NO. : 11,077,179 B2
APPLICATION NO. : 16/055565
DATED : August 3, 2021
INVENTOR(S) : Bruce S. Gillis It is certified that error appears in the above-identified patent and that said Letters Patent is hereby corrected as shown below:

In the Claims

At Claim 1, Column 27, Lines 20-21, please replace "wherein the *Mycobacterium* is *Mycobacterium bovis* (*M. bovis*), *Mycobacterium vaccae* (*M. vaccae*)" with --wherein the *Mycobacterium* is *Mycobacterium vaccae* (*M. vaccae*)--.

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*